(12) United States Patent
Flynn et al.

(10) Patent No.: US 7,273,577 B2
(45) Date of Patent: Sep. 25, 2007

(54) METHOD OF MANUFACTURING CATHETER

(75) Inventors: Kerry Flynn, Dunmore East (GB); Simon Andrews, Glasgow (GB)

(73) Assignee: Omega Critical Care Limited, Calderbank, Lanarkshire (GB)

( * ) Notice: Subject to any disclaimer, the term of this patent is extended or adjusted under 35 U.S.C. 154(b) by 136 days.

(21) Appl. No.: 10/494,142

(22) PCT Filed: Oct. 30, 2002

(86) PCT No.: PCT/GB02/04954

§ 371 (c)(1),
(2), (4) Date: Oct. 26, 2004

(87) PCT Pub. No.: WO03/037414

PCT Pub. Date: May 8, 2003

(65) Prior Publication Data

US 2005/0040557 A1 Feb. 24, 2005

(30) Foreign Application Priority Data

Oct. 31, 2001 (GB) ................................ 0126098.3

(51) Int. Cl.
*B29C 45/14* (2006.01)
(52) U.S. Cl. ...................... 264/261; 264/275; 264/277
(58) Field of Classification Search ................ 264/275, 264/277, 261
See application file for complete search history.

(56) References Cited

U.S. PATENT DOCUMENTS

| 4,636,272 | A | | 1/1987 | Riggs |
| 4,670,009 | A | * | 6/1987 | Bullock ...................... 604/533 |
| 5,380,301 | A | | 1/1995 | Prichard et al. |
| 5,895,695 | A | * | 4/1999 | Rowley ...................... 428/36.9 |
| 6,180,038 | B1 | * | 1/2001 | Cesaroni ...................... 264/135 |
| 6,290,265 | B1 | * | 9/2001 | Warburton-Pitt et al. 285/131.1 |
| 6,722,708 | B2 | * | 4/2004 | Morohoshi et al. ......... 285/423 |

FOREIGN PATENT DOCUMENTS

EP 0 322 225 6/1989

* cited by examiner

*Primary Examiner*—Edmund H. Lee
(74) *Attorney, Agent, or Firm*—Drinker Biddle & Reath

(57) ABSTRACT

The invention relates to a method of manufacturing a catheter, wherein the catheter comprises an elongate portion having a proximal end and at least one lumen at said proximal end, at least one extension tube having a passage, and a coupling element, the distal portion of the extension tube being capable of communicating with a lumen of the elongate portion via a passage in the coupling element wherein the method comprises a step wherein a removable insert element locates and holds the extension tube in contact with the elongate portion during the manufacture of a coupling element. The invention also relates to a removable insert for use in the manufacturing of catheters.

7 Claims, 6 Drawing Sheets

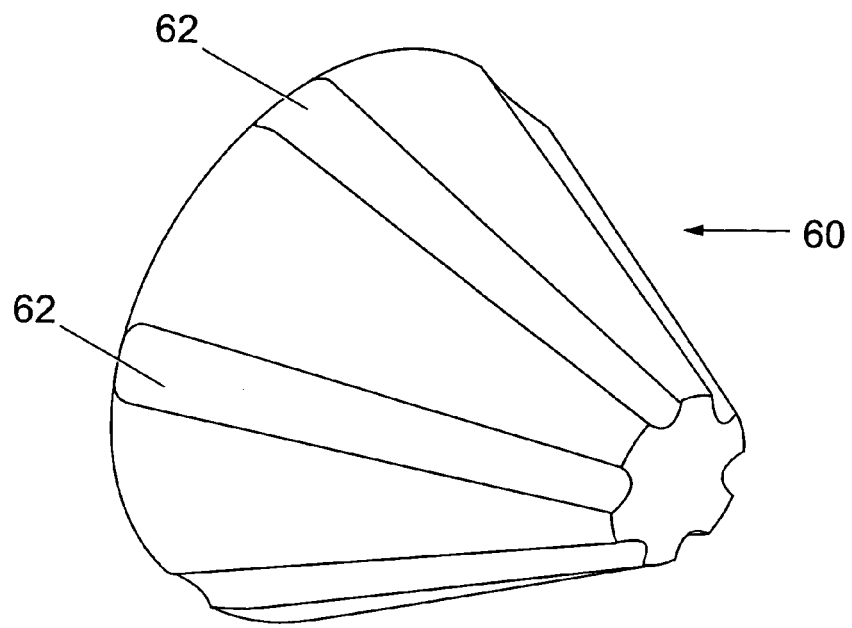
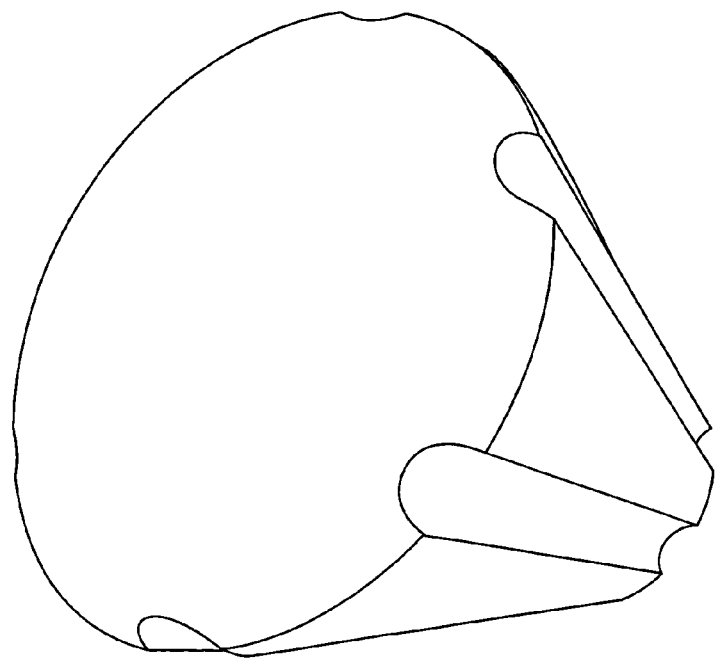
Fig. 8

METHOD OF MANUFACTURING CATHETER

The present invention relates to catheters which can be inserted into the human or animal body for various medical purposes. More particularly the present invention relates to catheters formed by moulding.

BACKGROUND OF THE INVENTION

A catheter includes an elongate slender flexible portion for insertion into a body cavity such as a vein or artery. The elongate portion has at least one lumen, but typically has a plurality of lumens, and extends from a proximal end at a coupling element to a distal end, which in use is inside the human or animal body. The lumens within the elongate portion can be used to introduce or remove fluid from the human or animal body or alternatively carry means allowing measurement of blood pressure, blood flow or such like. As each lumen typically contains different means performing different functions, the means within each lumen may be attached to particular components or equipment. The means within each lumen within the elongate portion are connected to particular components or equipment via extension tubes, which attach to the proximal end of the lumens of the elongate portion via the coupling element.

The extension tubes are commonly attached to the proximal end of the lumens of the elongate portion via plastic adapters. These plastic adapters may be glued in position using adhesive such that the adhesive bonds the extension tube to the elongate portion. However this method of gluing adapters to the extension tube is very labour intensive and requires long drying times for the adhesive to set and harden. Further, the adhesive may flow into one or more of the lumens of the elongate portion and completely or partially block the lumens.

An alternative method used, that eliminates the need for gluing, is the insertion of wire mandrels through an extension tube and into a lumen of the elongate portion. A mould tool is then placed around the elongate portion and extension tube and a coupling element formed by moulding plastic into the mould tool. The coupling element formed around the extension tube and the proximal end of the elongate portion, secures the extension tube to the elongate portion. Removal of the wire mandrels from the lumens of the elongate portion and from the extension tube creates passages in the coupling element allowing passage of fluid or other means from the extension tube into the lumens of the elongate portion.

This alternative method of attaching the extension tubes to the elongate member also has a number of disadvantages in that large diameter extension tubes or elongate portions tend to melt in the mould, while small diameter extension tubes or elongate portions allow the plastic being moulded to "flash" out of the mould alongside the extension tubes or elongate portions. In addition the hot plastic used for moulding can cause kinking or collapse of the lumens within the elongate portion.

The moulding method described above to attach the extension tubes to the elongate portion has been improved by including an insert element in the catheter as described in U.S. Pat. No. 4,670,009. The insert element of the catheter surrounds the extension tubes, holding the extension tubes in place in the finished catheter and preventing the injected plastic from "flashing" out around the extension tubes during the moulding process. During manufacture the use of an integral insert element in the catheter means the mould need not be sized to accommodate any particular number or diameter of extension tubes, provided the mould can close off around the insert element such that no plastic flashes through the moulding insert interface.

The use of an insert element which is incorporated into the final catheter product to secure the extension tubes to the elongate element requires that the integral insert element is pre-fabricated for each catheter being produced. The fabrication of an integral insert element adds to the cost of the production of the catheter. Further the use of an integral insert element in the catheter adds to the number of components and material within the catheter and this again contributes to the production cost of the catheter.

It would be advantageous if a catheter could be produced which did not require an integral insert element to be fabricated for and included in each catheter produced. The use of a releasable insert element(s) or an insert element integral to the mould tool would be advantageous as the use of such an insert would reduce the expense of fabrication of the catheter and further reduce the cost of the material required to make the catheter.

SUMMARY OF THE INVENTION

According to the present invention there is provided a method of manufacturing a catheter wherein the catheter comprises an elongate portion having a proximal end and at least one lumen at said proximal end, at least one extension tube having a passage, and a coupling element, the distal portion of the extension tube being capable of communicating with a lumen of the elongate portion via a passage in the coupling element wherein the method comprises the use of a removable insert element to locate and hold the extension tube during the manufacture of coupling element.

The invention further provides a catheter made according to this method.

Accordingly the invention provides a removable insert to locate and hold at least one extension tube during the manufacture of a catheter.

Preferably the removable insert element is comprised of metal, composite, or high melting temperature plastic.

Preferably the removable insert element is capable of being positioned in the mould tool to locate the extension tubes within the coupling element.

Preferably the removable insert element is formed of a single section.

Alternatively the removable insert element is formed by a plurality of sections.

Preferably the coupling element includes plastic material which is moulded over the elongate element.

Preferably the catheter comprises a plurality of extension tubes and the elongate portion comprises a plurality of lumens, the passages of extension tubes corresponding with the respective lumens of the elongate portion.

Alternatively the catheter comprises a plurality of extension tubes and the elongate portion comprises a plurality of lumens, wherein a passage of an extension tube corresponds with at least two lumens of the elongate portion.

Preferably the passages in the coupling element are formed using wire mandrels extending from the extension tubes into the lumen of the elongate portion.

Preferably the elongate portion is flexible and sized to be received within the vein or artery.

Prefereably the removable insert element provides a recess volume in the coupling element to accept an extension tube.

Alternatively the removable insert element may create a feature to connect at least one extension tube to at least one lumen of the elongate portion.

Preferably a mandrel guide is used to position the wire mandrels extending from an extension tube into a lumen of the elongate portion.

Preferably a mandrel guide is used to position the wire mandrels in combination with a releasable insert element.

Preferably the mandrel guide has locating features on a first end wherein the locating features are capable of locating the mandrel guide in a particular orientation relative to the removable insert element.

BRIEF DESCRIPTION OF THE DRAWINGS

An embodiment of the present invention will now be described by way of example only with reference to the accompanying drawings in which FIG. 8 shows an alternative mandrel guide.

DETAILED DESCRIPTION OF THE PREFERRED EMBODIMENTS

Figure 1:
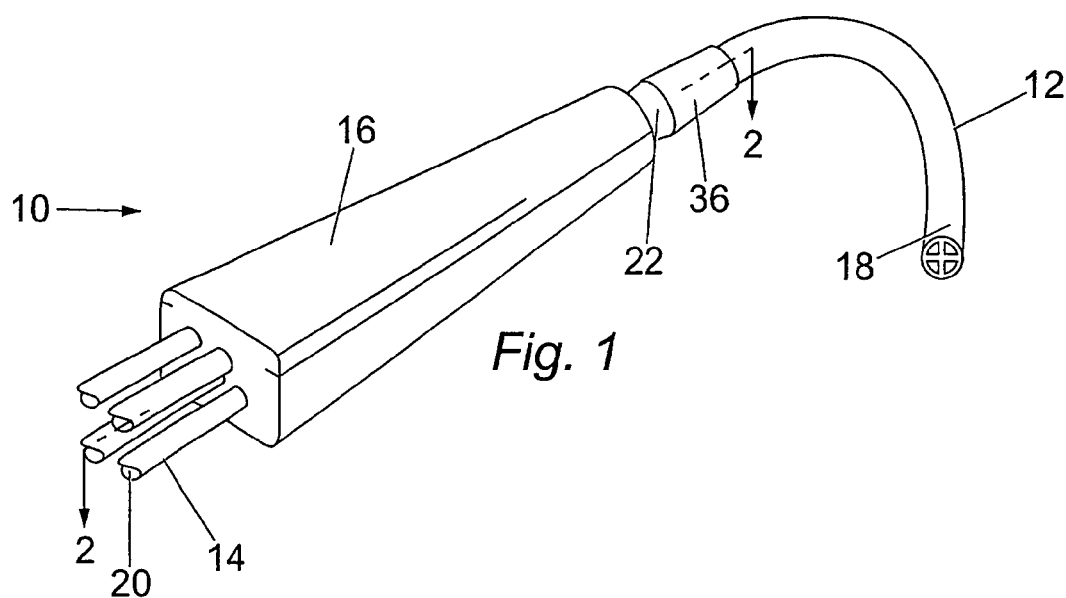
FIG. 1 is an isometric view of the catheter.

FIG. 1 shows a catheter 10 which comprises an elongate portion 12, extension tubes 14, and a connecting element 16. The connecting element 16 receiving at least part of the extension tube 14 and the elongate portion 12 such that it is capable of retaining these within the connecting element 16.

In the embodiment shown in FIG. 1 the elongate portion 12 comprises four lumens 18 although different elongate portions could contain greater or fewer numbers of lumens. In the embodiment shown in FIG. 1 each of the lumens 18 of the elongate portion 12 correspond to a distinct passage 20 of an extension tube 14. Each particular extension tube 14 may be connected to different pieces of equipment (not shown) to allow each of the lumens 18 to contain different elements such as conductive wires, thermistors, pressure sensing apparatus, means for infusing solutions or the like.

The elongate portion 12 may be constructed of a biocompatible plastic material such as PVC, the proximal end 22 of the elongate portion 12 being received by the coupling means 16. The extension tubes 14 may be of equal or different diameter to each other and may be constructed of a suitable plastics material such as PVC.

Figure 2:
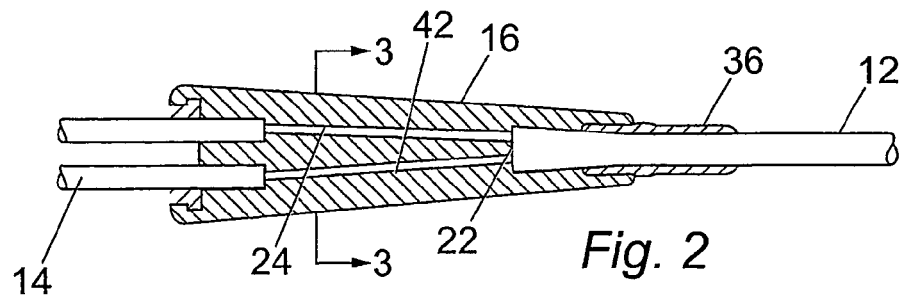
FIG. 2 is a sectional view of the catheter along line 2-2.
Figure 3:
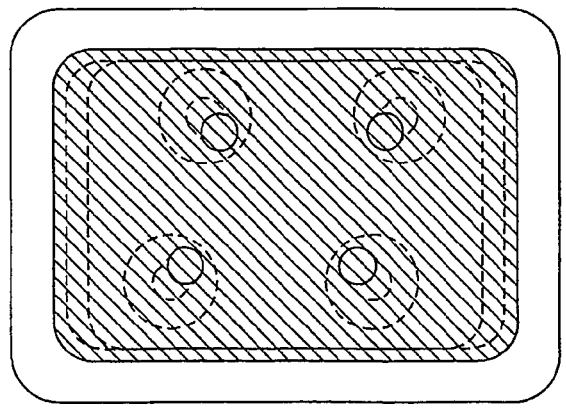
FIG. 3 is an enlarged sectional view along line 3-3, FIGS. 4a and b are isometric drawings depicting the main steps involved in forming the catheter.

The coupling element 16 is also constructed of a suitable plastics material such as polyester or low melting temperature plastic, metal or composite, which allows it to be bonded to the plastic of the elongate portion 12 and the extension tubes 14 during the moulding process. As shown in FIG. 2 wire mandrels 24 are passed through the passages 20 of the extension tubes 14 into the lumens 18 of the elongate portion 12 such that during the moulding process they are able to form passages 42 in the coupling element linking the elongate portion 12 to the extension tubes 14.

Moulding of the coupling element may be performed by any means known in the art including introducing powdered plastic into the mould tool and heating the mould or injecting plastic into the mould tool. In the embodiment described injection moulding is the preferred method of forming the coupling element.

During the moulding process a removable insert 28 is used to hold the extension tubes 14 in place within the coupling means 16 and prevent the plastic from flashing out of the mould at the position at which the extension tubes exit the mould tool 32.

The removable insert element 28 may be constructed of metal, composite or a suitable high melt plastic. The removable insert element comprises at least one passage 34. In the embodiment shown four passages are present that extend through the removable insert element 28 from a first face of the removable insert element 28, which faces the elongate element to a second opposite face. The passage 34 through the removable insert element 28 is sized such that it grips extension tube 14 pushed through the passage 34 of the removable insert element 28. Further the removable insert element 28 may comprise a flange portion 29 to aid location of the removable insert element 28 in the mould tool 32.

Figure 4:
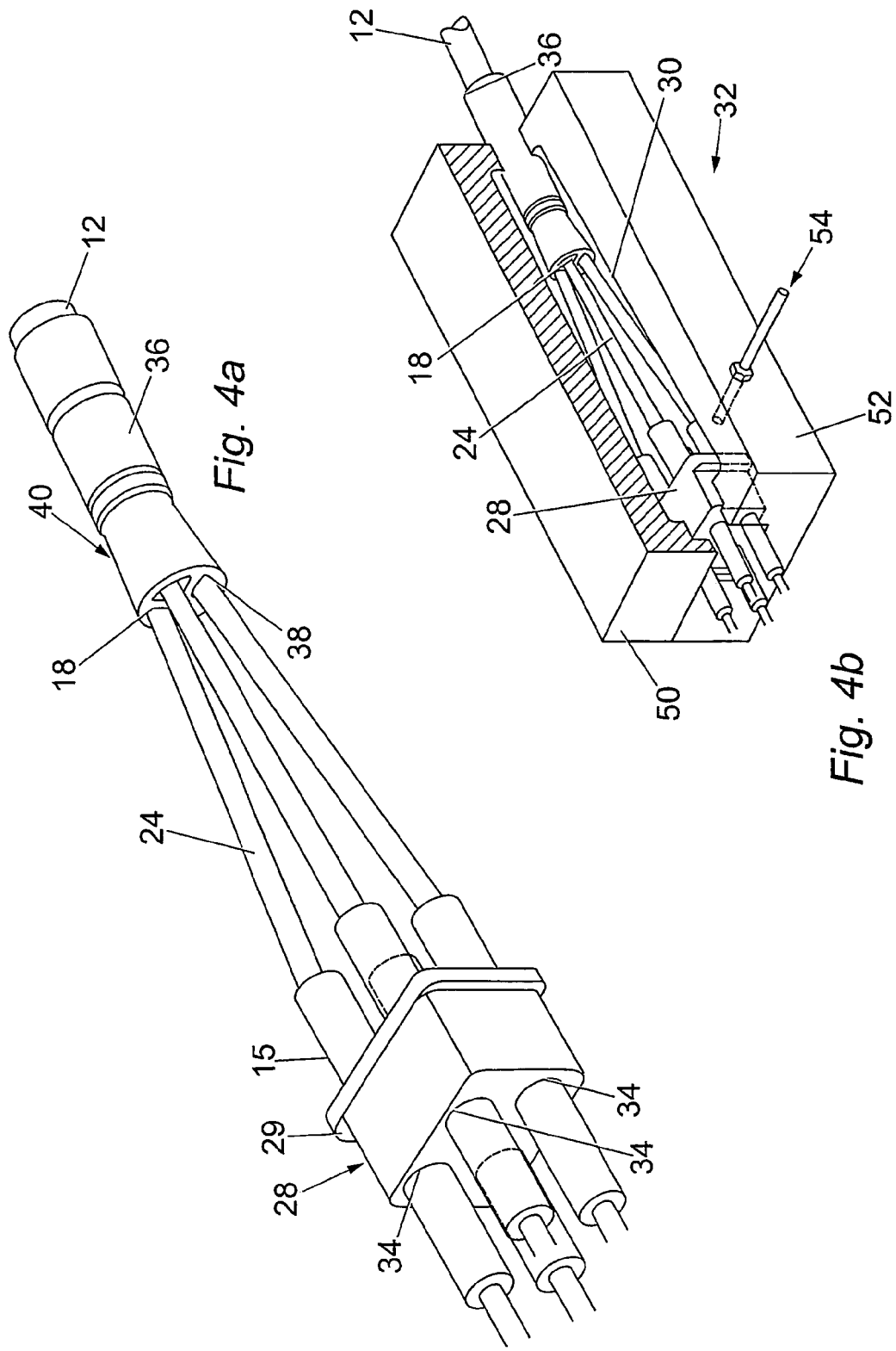
Figure 5:
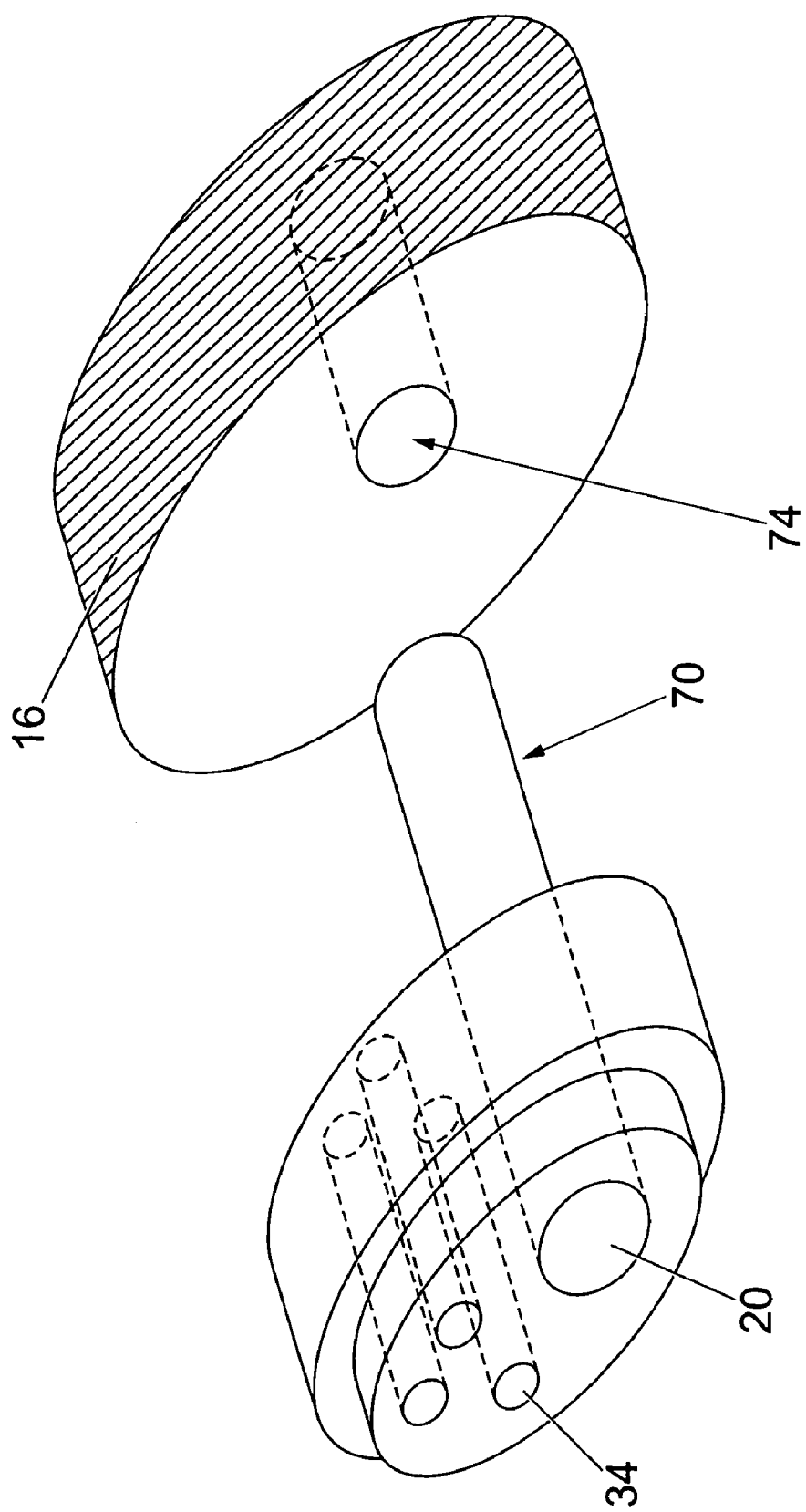
FIG. 5 shows a removable insert able to create a recess volume in the connecting element to accept an extension tube.
Figure 6:
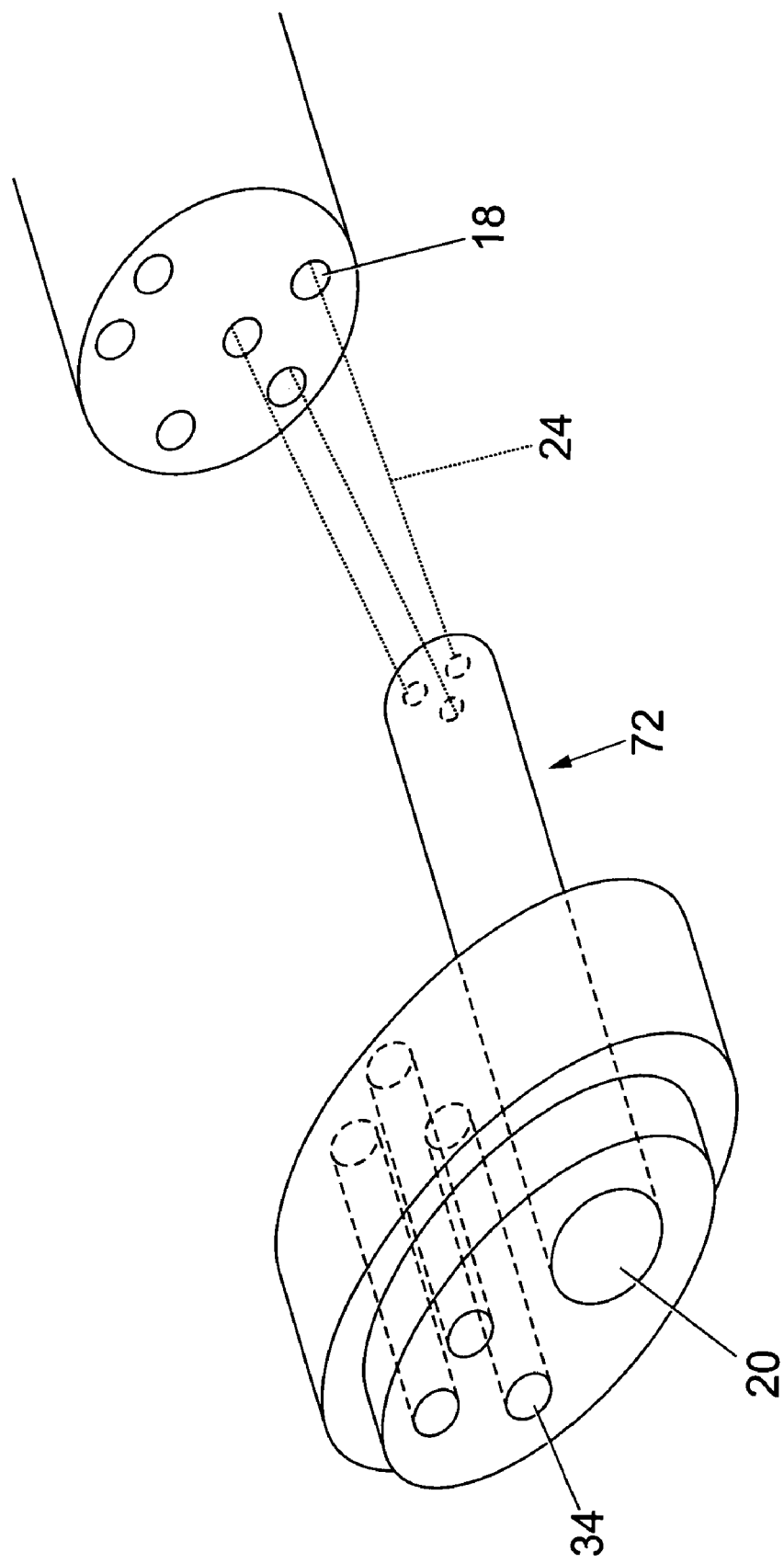
FIG. 6 shows a removable insert able to connect an extension tube to more that one lumen of the catheter body.

As shown in FIGS. 4 and 5 the preferred method of manufacturing the catheter is a predetermined portion 15 of at least one extension tube 14 is passed through the passage 34 of the removable insert element 28 such that the portion 15 of the extension tube 14 extends beyond the second face of the removable insert element 28 such that when the removable insert element 28 is located within the mould tool 32, the portion 15 of the extension tube 14 which extends beyond the removable insert element 28 enters into the space 30 within the mould tool 32 into which the plastic is to be injected or entered into the mould.

As the extension tubes 14 are frictionally held within the passages 34 of the removable insert element 28 when the removable insert element is located within the mould tool 32, the extension tubes 14 are suitably located in the coupling element 16 when it is formed by the moulding process.

The elongate portion 12 is located and held by the coupling element 16 using a sleeve 36. The sleeve 36 is a thin walled flexible tube, capable (using its inner face 38) of tightly gripping the outer face of the proximal end of the elongate portion 12.

The sleeve 36 being attached to the connecting element 16 via its outer face 40 during the moulding process.

During the manufacture of the catheter the sleeve 36 containing the elongate portion is suitably positioned in the mould tool 32 such that the coupling element can be around it.

The sleeve 36 is pliable such that it is able to take up variances in the diameter of the elongate portion 12 created during the production of the elongate portion 12.

Wire mandrels 24 are inserted through the extension tubes 14 and into the respective lumens 18 of the elongate portion where they are held in place by friction. Removal of the wire mandrels 24, following moulding enables passages through the coupling element 16 to be created.

As shown in FIG. 4b the mould tool 32 comprises sections 50 and 52 which can be moved relative to each other away from each other to an open position or toward each other to a closed position. In the open position the removable insert element 28 can be located within the mould tool 32. The sleeve 36 can also be positioned in the mould tool 32, the sleeve 36 gripping the proximal end of the elongate tube 12 such that it will be suitably located within the coupling element 16 when the coupling element is formed by the moulding process.

Once the removable insert element 28 and sleeve 36 have been located in the mould tool, mould tool sections 50 and 52 can be moved to a closed position such that the mould tool 32 forms a tight fit around the removable insert element 28. Further the closed mould tool has a tight fit around the sleeve 36.

When the mould tool sections 50 and 52 are in the closed position, hot plastic may be injected or entered into the space 30 via inlet 54 to form the connecting element 16. The tight fit of the removable insert element 28 ensures that no plastic flashes out around the removable insert element 28, while the tight fit of the mould tool 32 around the sleeve 36 ensures that plastic cannot flash out between the mould tool 32 and the sleeve 36.

The grip of the sleeve 36 on the elongate portion 12 further ensures that plastic cannot flash out between the sleeve 36 and the elongate portion 12.

The plastic of the coupling element 16 forms around the portion 15 of the extension tubes 14, which extends beyond the removable insert means 28 into the cavity 30, and the sleeve 36, which grips the elongate portion 12. Once cured the plastic which forms the coupling element therefore holds the extension tubes 14 and the sleeve 36 in the coupling element 16, but does not grip or attach the removable insert element 28.

The injected plastic and plastic entered into the mould tool flows around the wire mandrels 24 causing the mandrels when removed to leave passages 42 through the coupling element. After the plastic of the coupling element cures the mould sections 50 52 can be relatively moved away from each other to an open position. The extension tubes 14 are pulled through the passages of the removable insert element 28 and the catheter including extension tubes 14, wire mandrels 24, connecting element 16, sleeve 36 and elongate member 12 can be removed from the mould. The removable insert means may then be reused to hold extension tubes to form a second or subsequent catheter, saving on material and production costs of insert elements.

The wire mandrels 24 can then be removed from the extension tubes 14 and lumens 18 of the elongate portion 12 to form passages 42 in the coupling element 16.

In an alternative embodiment of the present invention the wire mandrels 24 may be held in position within the mould tool 32 by a mandrel guide member 60. This mandrel guide member 60 can be of any suitable shape such that it can be positioned between the wire mandrels 24. The mandrel guide member 60 having a series of grooves 62 around its perimeter in which the wire mandrels 24 can be located to suitably position them in the coupling element 16.

The mandrel guide member 60 prevents the wire mandrels 24 touching each other and thereby prevents interpassage leaks in the coupling element 16.

Figure 7:
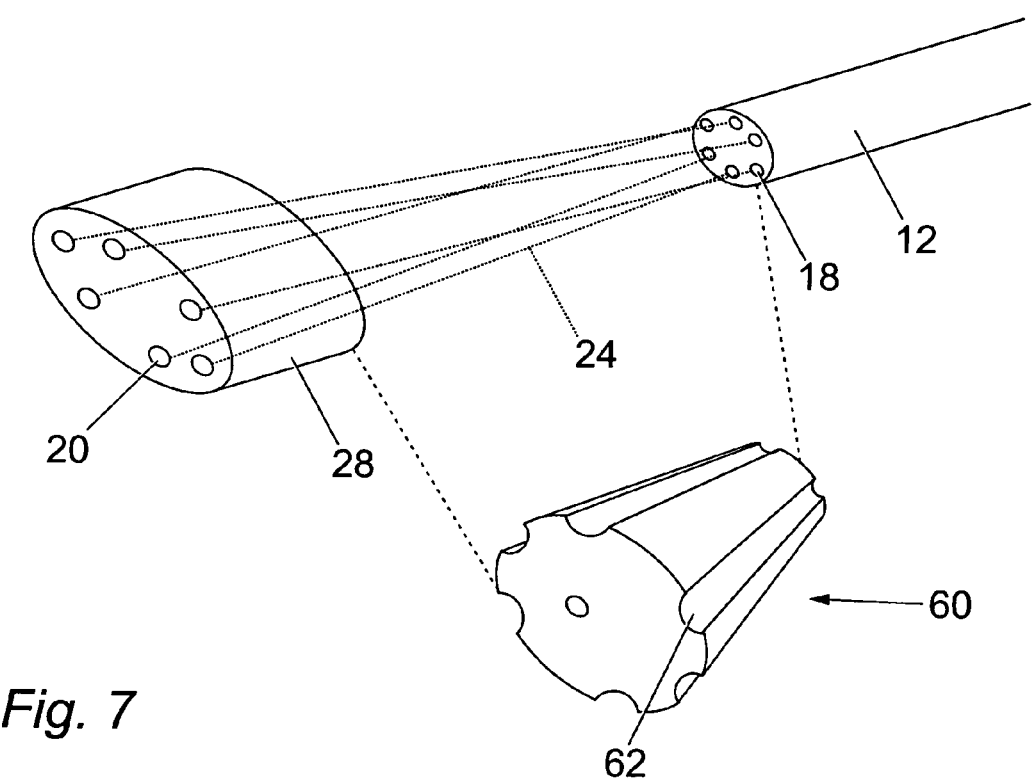
FIG. 7 shows a mandrel guide.

As shown in FIGS. 7 and 8 the mandrel guide may be cylinder shaped or cone shaped depending on how the mandrels are to be arranged.

Various embodiments of the present invention can be envisaged without departing from the scope of the present invention. For example the removable insert element 28 may be shaped as shown in FIG. 5 with a protrusion 70 extending from the surface of the removable insert element 28 which contacts the coupling element during moulding. This protrusion 70 may be used to create a recess volume 74 in the coupling element 16, this recess volume 74 providing a feature which allows the attachment of an extension tube 12 at a period after formation of the coupling element 16.

Alternatively the removable insert element 28 may be shaped such that it is able to connect one extension tube to more than one lumen in the elongate member. As shown in FIG. 5, a larger passage 72 may be created in the removable insert element 28 able to accommodate an extension tube into which a plurality of mandrels linking to a plurality of lumens 18 in the elongate portion 12 can be placed.

The invention claimed is:

1. A method of manufacturing a catheter wherein the catheter comprises an elongate portion having a proximal end and at least one lumen at said proximal end, at least one extension tube having a passage, and a coupling element, the distal portion of the extension tube being capable of communicating with a lumen of the elongate portion via a passage in the coupling element wherein the method comprises:

providing a removable insert element wherein said removable insert element locates and holds the extension tube during the manufacture of the coupling element;

inserting a wire mandrel through an extension tube and into a lumen of the elongate portion;

positioning the removable insert in a mold tool to locate the extension tube within the coupling element such that plastic is prevented from flashing out of the mold at the portion at which the extension tube exits the mold;

forming the coupling element in the mold tool wherein the removable insert is positioned in the mold tool to locate the extension tube within the coupling element; and removing:

(i) the wire mandrel from the lumen of the elongate portion and from the extension tube to create a passage in the coupling element from the extension tube into the lumen of the elongate portion; and (ii) the removable insert element from the coupling element.

2. The method as claimed in claim 1, further comprising fabricating the removable insert from one of a metal, composite, and high melting temperature plastic material.

3. The method as claimed in claim 1, further comprising locating the removable insert to provide at least one recess volume in the coupling element to accept an extension tube.

4. The method as claimed in claim 1, further comprising providing the removable insert element with means to connect at least one extension tube to at least one lumen of the elongate portion of a catheter.

5. The method as claimed in claim 1, wherein a mandrel guide is used to position the wire mandrel extending from an extension tube into a lumen of the elongate portion.

6. The method as claimed in claim 1, wherein a mandrel guide is used to position the wire mandrel in combination with the removable insert element.

7. The method as claimed in claim 6, further comprising providing the mandrel guide with locating features on a first end, the locating features being capable of locating the mandrel guide in a particular orientation relative to the removable insert element.

* * * * *